United States Patent [19]

Ribaldone

[11] 3,943,136
[45] Mar. 9, 1976

[54] PROCESS FOR PREPARING 3,3-THIOBIS (2-METHOXY-1-AZABENZANTHRONE

[75] Inventor: Giuseppe Ribaldone, Gallarate, Italy

[73] Assignee: Montedison S.p.A.,, Milan, Italy

[22] Filed: Aug. 21, 1974

[21] Appl. No.: 499,416

[30] Foreign Application Priority Data
Aug. 22, 1973  Italy.................................. 28086/73

[52] U.S. Cl. ............................................... 260/272
[51] Int. Cl.² ........................................ C07D 221/18
[58] Field of Search............................. 260/272, 278

[56] References Cited
UNITED STATES PATENTS
3,242,184   3/1966   Moser et al.......................... 260/272

3,678,053   7/1972   Boffa et al. .......................... 260/278

Primary Examiner—Richard J. Gallagher

[57] ABSTRACT

A new process for preparing 3,3 - thio - bis[2-Methoxy-1-azabenzanthrone], a useful intermediate in the synthesis of dyestuffs, is disclosed. The process involves reacting 2-methoxy-1-azabenzanthrone with sulfur chlorides in suspension or solution in an inert solvent under heating, and recovering the reaction product from the reaction mass, e.g., by filtering.

8 Claims, No Drawings

PROCESS FOR PREPARING 3,3-THIOBIS (2-METHOXY-1-AZABENZANTHRONE

BACKGROUND OF THE INVENTION

It is known from Italian Pat. Nos. 869,691 and 901,929 assigned to Montedison, that an excellent bright blue vat dye containing the structure of 5, 14-diazaisoviolanthrone can be obtained from 3,3'-thiobis [2-methoxy-1-azabenzanthrone] by alkaline fusion.

According to Italian Pat. No. 869,691, 3,3'-thiobis[2-methoxy-1-azabenzanthrone] was synthesized by bromination of 2-hydroxy-1-azabenzanthrone in $H_2SO_4$, methylation of the resulting 3-bromine-2-hydroxy-1-azabenzanthrone with $(CH_3)_2SO_4$, and subsequent reaction of the methylated compound with $Na_2S$:

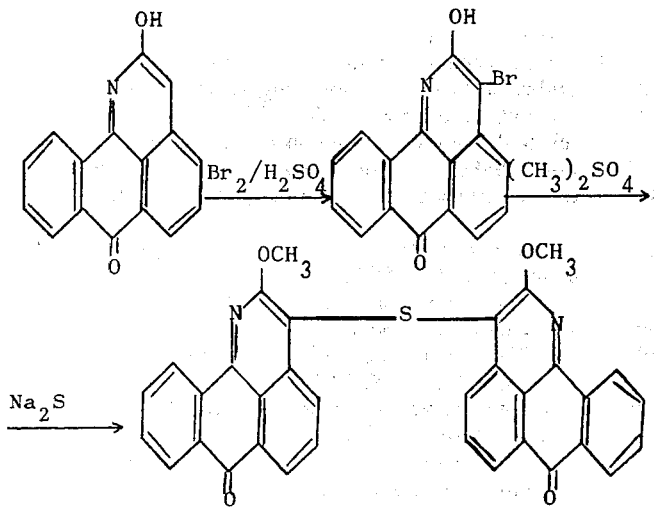

THE PRESENT INVENTION

We have found that 3,3'-thiobis[2-methoxy-1-azabenzanthrone] can be obtained in better yields and with fewer steps by reacting the methylation product of 2-hydroxy-1-azabenzanthrone, that is 2-methoxy-1-azabenzanthrone, with sulphur chlorides.

The sulphur halides used in the process of this invention are sulfur monochloride, $S_2Cl_2$, and sulfur dichloride, $SCl_2$. As is obvious, when sulfur dichloride ($n = 1$) is used in the reaction, no sulfur is liberated.

The reaction proceeds as follows:

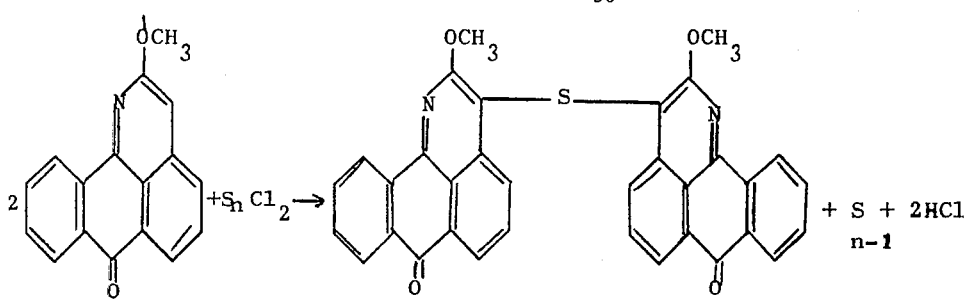

wherein $n = 1$ or 2.

In general, the process of this invention is carried out as follows: First, there is prepared a suspension or solution of 2-methoxy-1-azabenzanthrone in an inert solvent chosen from among the group of chlorinated saturated aliphatic hydrocarbons like methylene chloride, chloroform, carbon tetrachloride, dichloroethane, tetrachloroethane, or from other inert solvents like dimethyl formamide and nitrobenzene.

Sulfur chloride is then added and the whole is heated to 40° – 100°C, preferably to 50° – 80°C.

Upon completion of the reaction, the reaction mixture appears to be heterogeneous, insofar as the formed 3,3'-thiobis[2-methoxy-1-azabenzanthrone] is very little soluble in the solvents employed. After cooling, the reaction product is filtered, washed with the reaction solvent, or with another solvent such as ethyl ether, petroleum ether, acetone or benzene, and dried.

The mother liquors can be recycled to another operation.

The amount of sulfur chloride used is from 0.5 to 5 mols of sulfur chloride/mol of 2-methoxy-1-azabenzanthrone, preferably from 0.5 to 1.0 mols. The reaction time ranges from 1 to 10 hours, depending on the reaction temperature, on the solvent, on the amount and type of sulfur chloride employed.

The following examples are given to illustrate the invention and are not, or intended to be, limiting.

EXAMPLE 1

200 g of 2-hydroxy-1-azabenzanthrone, 68.4 g of 85% KOH and 7 liters of water are introduced into a beaker, then the whole is heated under stirring to 50°C until a solution is obtained. The whole is cooled to 25°C, 65 g of 85% KOH are added and 288 g of dimethyl sulfate are fed in over a period of 1.5 h and stirring is continued at 25°C for another 1.5 h. The reaction mixture, which now contains the formed 2-methoxy-1-azabenzanthrone in suspension and which shows an almost neutral reaction, is alkalinized with 100 cc of 10% NaOH and heated to 55° – 60°C. The whole is filtered in the hot state, the solid is washed with hot water up to neutrality, then dried at 100°C until a constant weight is obtained. 204 g of 2-methoxy-1-azabenzanthrone corresponding to a yield of 96.5% are obtained.

After crystallization from dimethyl formamide or ethanol, the product appears in the form of yellowish crystals and melts at 190° – 192°C. The elemental analysis and IR spectrum are in accordance with the structure of the compound.

80 g of 2-methoxy-1-azabenzanthrone, 480 cc of dichloroethane and 25 g of $S_2Cl_2$ (sulfur monochloride) are fed into a flask equipped with a thermometer, a stirrer and a reflux cooler. The thus obtained suspension is heated under stirring for 5 hours to 50°C and then for 3 hours to the boiling temperature (internal temperature 78° – 80°C). Upon completion of the reaction the whole is cooled to room temperature and filtered, the solid is washed with dichloroethane and ether, then the whole is dried at 100°C until a constant weight is obtained. 80.8 g of 3,3-thiobis [2-methoxy-1-azabenzanthrone] corresponding to a yield of 95.5% are obtained.

After crystallization from nitrobenzene or ortho-dichlorobenzene, the product appears in the form of crystals having a yellow-orange color and melts at 366° – 368°C. The elemental analysis and the IR spectrum are in compliance with the structure of the compound.

EXAMPLES 2 – 6

The following table reports the reaction conditions and yields of 3,3'-thiobis-2-methoxy-1-azabenzanthrone (TMAB) obtained in some runs effected by reacting 2-methoxy-1-azabenzanthrone (MAB) with $S_2Cl_2$ or $SCl_2$ in various solvents. The operating modalities and equipment used are those described in Example 1.

| MAB g | Sulfur chloride | g | Solvent | cc. | Reaction conditions | MAB obtained g | yield % |
|---|---|---|---|---|---|---|---|
| 10 | $S_2Cl_2$ | 2.84 | dichloroethane | 100 | 2h at 50° and 4h at 80°C | 9.34 | 88.3 |
| 10 | $S_2Cl_2$ | 2.84 | tetrachloroethane | 60 | 5h at 50° and 5h at 80°C | 9.10 | 86.0 |
| 10 | $S_2Cl_2$ | 3.1 | nitrobenzene | 60 | 5h at 50° and 3h at 80°C | 10.10 | 95.5 |
| 10 | $SCl_2$ | 4.0 | nitrobenzene | 60 | 9h at 50°C | 9.50 | 89.8 |
| 10 | $SCl_2$ | 3.0 | dichloroethane | 100 | 5h at 80°C | 9.00 | 85.1 |

What I claim is:

1. A process for preparing 3,3-thiobis [2-methoxy-1-azabenzanthrone], comprising reacting 2-methoxy-1-azabenzanthrone with sulfur chlorides in inert solvents selected from the group consisting of chlorinated saturated aliphatic hydrocarbons $C_1 - C_2$, dimethylformamide and nitrobenzene, at a temperature of from 40° to 100°C.

2. The process according to claim 1, in which the sulfur chloride is $SCl_2$.

3. The process according to claim 1, in which the sulfur chloride is $S_2Cl_2$.

4. The process according to claim 1, in which the reaction solvent is $CH_2Cl_2$.

5. The process according to claim 1, in which the reaction solvent is $CHCl_3$.

6. The process according to claim 1, in which the reaction solvent is $CCL_4$.

7. The process according to claim 1, in which the reaction solvent is $C_2H_4Cl_2$.

8. The process according to claim 1, in which the reaction solvent is tetrachloroethane.

* * * * *

UNITED STATES PATENT OFFICE
CERTIFICATE OF CORRECTION

Patent No. 3,943,136     Dated March 9, 1976

Inventor(s) Giuseppe RIBALDONE

It is certified that error appears in the above-identified patent and that said Letters Patent are hereby corrected as shown below:

Covering page, Item [54]

"Process For Preparing 3,3-Thiobis (2-Methoxy-1-Azabenzanthrone"

should be - - - Process For Preparing 3,3'-Thiobis [2-Methoxy-1-Azabenzanthrone]

Signed and Sealed this

Seventh Day of March 1978

[SEAL]

Attest:

RUTH C. MASON
Attesting Officer

LUTRELLE F. PARKER
Acting Commissioner of Patents and Trademarks